(12) United States Patent
Begin et al.

(10) Patent No.: US 11,533,949 B2
(45) Date of Patent: Dec. 27, 2022

(54) AEROSOL PROVISION SYSTEM AND REMOVABLE MEMBER

(71) Applicant: Nicoventures Trading Limited, London (GB)

(72) Inventors: Mark Begin, Madison, WI (US); Steve Dieter, Madison, WI (US); David Christian Eby, Madison, WI (US); Greg Falendysz, Madison, WI (US); Mark Forster, London (GB); Kaya Ouchi, London (GB); Benjamin J. Paprocki, Madison, WI (US)

(73) Assignee: Nicoventures Trading Limited, London (GB)

( * ) Notice: Subject to any disclaimer, the term of this patent is extended or adjusted under 35 U.S.C. 154(b) by 213 days.

(21) Appl. No.: 16/758,975

(22) PCT Filed: Oct. 24, 2018

(86) PCT No.: PCT/US2018/057344
§ 371 (c)(1),
(2) Date: Apr. 24, 2020

(87) PCT Pub. No.: WO2019/084161
PCT Pub. Date: May 2, 2019

(65) Prior Publication Data
US 2020/0345960 A1  Nov. 5, 2020

(30) Foreign Application Priority Data

Oct. 24, 2017 (GB) .................... 1717476

(51) Int. Cl.
*H01R 13/60* (2006.01)
*A24F 40/40* (2020.01)
(Continued)

(52) U.S. Cl.
CPC ........... *A24F 40/40* (2020.01); *A61M 11/042* (2014.02); *A61M 15/06* (2013.01); *A24F 40/20* (2020.01);
(Continued)

(58) Field of Classification Search
CPC .......... A24F 40/40; A24F 40/20; A24F 40/42; A24F 40/465; A61M 11/042; A61M 15/06; A61M 2205/8206; H05B 2203/021
(Continued)

(56) References Cited

U.S. PATENT DOCUMENTS 5,181,626 A    1/1993  Daenen
2016/0270438 A1  9/2016  Jackson
(Continued)

FOREIGN PATENT DOCUMENTS

CN    204232280    4/2015
CN    106723 3 81   5/2017
(Continued)

OTHER PUBLICATIONS

International Search Report, Application No. PCT/US2018/057344, dated Feb. 19, 2019, 3 pages.
(Continued)

*Primary Examiner* — Khiem M Nguyen
(74) *Attorney, Agent, or Firm* — Patterson Thuente, P.A.

(57) ABSTRACT

In one aspect, an aerosol provision system is provided. The system includes an assembly defining an opening configured to receive a replaceable consumable and a removable member releasably engaged with the assembly. The removable member is configured to form part of an outer surface of the system, and is positioned so as not to obstruct the opening.

20 Claims, 13 Drawing Sheets

(51) Int. Cl.
  *A61M 11/04* (2006.01)
  *A61M 15/06* (2006.01)
  *A24F 40/465* (2020.01)
  *A24F 40/42* (2020.01)
  *A24F 40/20* (2020.01)

(52) U.S. Cl.
  CPC ............ *A24F 40/42* (2020.01); *A24F 40/465* (2020.01); *A61M 2205/8206* (2013.01); *H05B 2203/021* (2013.01)

(58) Field of Classification Search
  USPC ........................................................ 131/329
  See application file for complete search history.

(56) References Cited

U.S. PATENT DOCUMENTS

| | | | |
|---|---|---|---|
| 2017/0181471 A1 | 6/2017 | Phillips et al. | |
| 2021/0007413 A1* | 1/2021 | Moloney | A61M 15/06 |
| 2021/0022395 A1* | 1/2021 | Moloney | A24F 40/40 |
| 2021/0030059 A1* | 2/2021 | Moloney | A24F 40/51 |
| 2021/0212370 A1* | 7/2021 | Moloney | A24F 40/42 |

FOREIGN PATENT DOCUMENTS

| | | |
|---|---|---|
| CN | 106617324 | 5/2017 |
| CN | 206482013 | 9/2017 |
| EP | 2779851 A2 | 9/2014 |
| GB | 2534213 | 7/2016 |
| KR | 20150022127 A | 3/2015 |
| KR | 20160116991 | 10/2016 |
| WO | WO 2013/102611 | 7/2013 |
| WO | WO 2014020953 | 2/2014 |
| WO | WO 2016207407 | 12/2016 |
| WO | WO 2017194763 | 11/2017 |

OTHER PUBLICATIONS

Great Britain Search Report, Application No. GB 1717476.4, dated Apr. 24, 2018, 6 pages.

International Preliminary Report on Patentability for Application No. PCT/US2018/057344, dated May 7, 2020, 8 pages.

Office Action for Korean Application No. 10-2020-7013728, dated May 17, 2022, 15 pages.

* cited by examiner

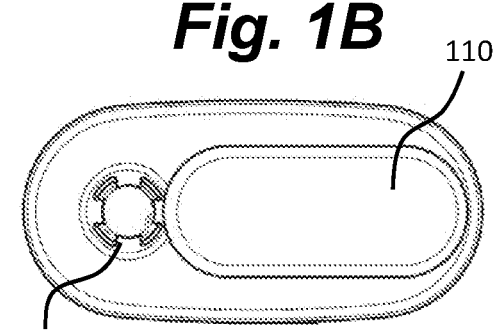
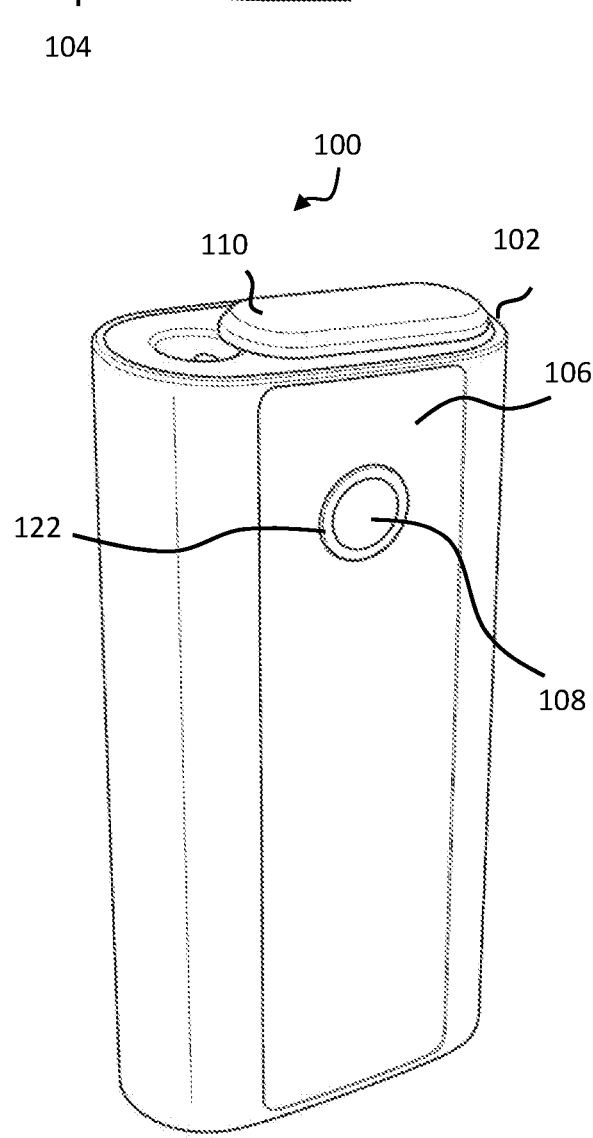
Fig. 1A
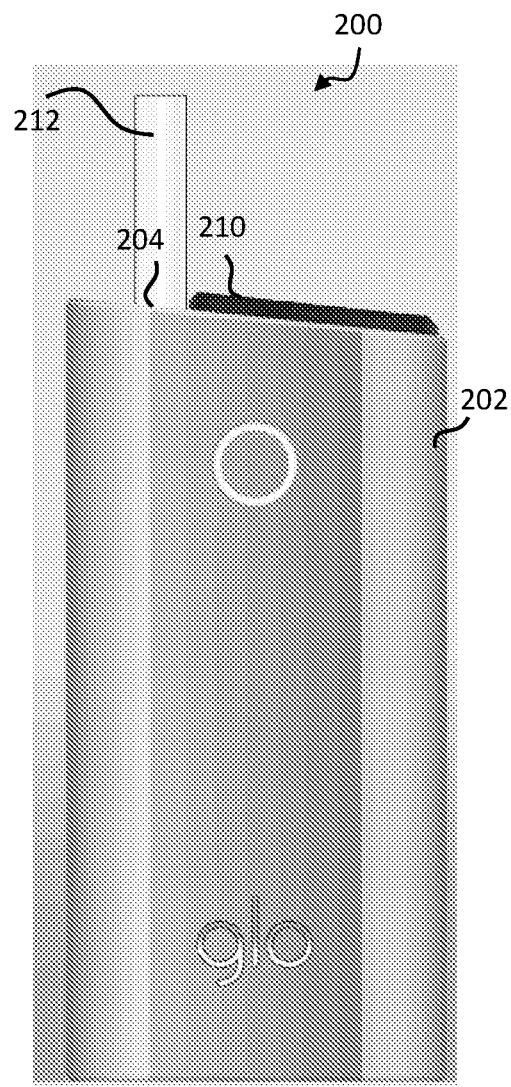
Fig. 2

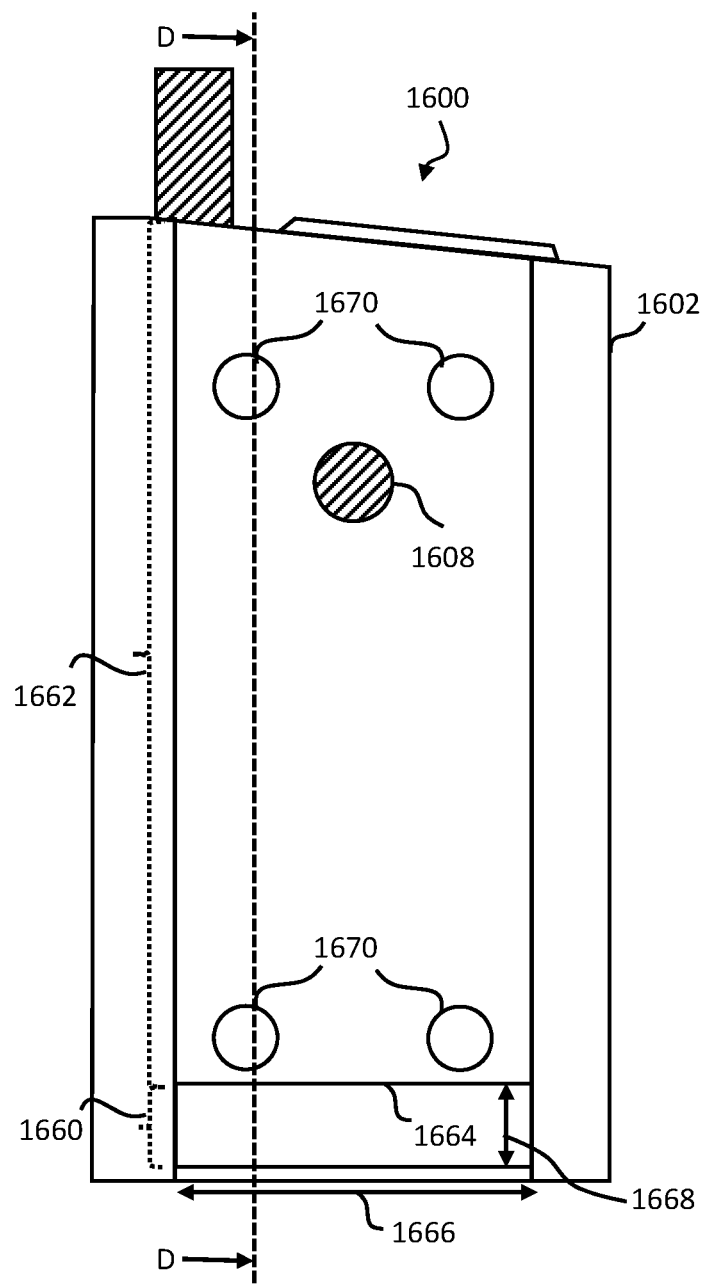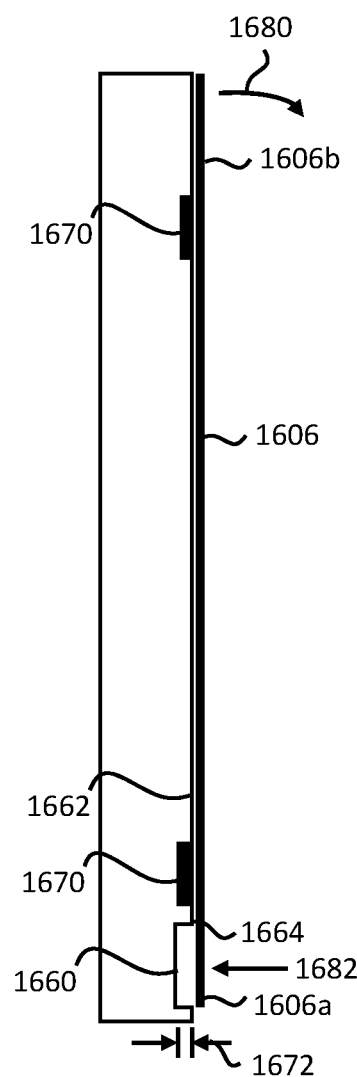
*Fig. 16*  *Fig. 17*

AEROSOL PROVISION SYSTEM AND REMOVABLE MEMBER

PRIORITY CLAIM

The present application is a National Phase entry of PCT Application No. PCT/US2018/057344, filed Oct. 24, 2018, which claims priority from GB Application No. GB1717476.4, filed Oct. 24, 2017, each of which is hereby fully incorporated herein by reference.

TECHNICAL FIELD

The present disclosure relates to an aerosol provision system and a removable member therefor.

BACKGROUND

Smoking articles such as cigarettes, cigars and the like burn tobacco during use to create tobacco smoke. Attempts have been made to provide alternatives to these articles that burn tobacco by creating products that release compounds without burning. Examples of such products are heating devices which release compounds by heating, but not burning, the material. The material may be for example tobacco or other non-tobacco products, which may or may not contain nicotine.

SUMMARY

According to a first aspect of the present disclosure, there is provided an aerosol provision system, comprising: an assembly defining an opening configured to receive a replaceable consumable; and a removable member releasably engaged with the assembly, the removable member configured to form part of an outer surface of the system, and positioned so as not to obstruct the opening.

According to a second aspect of the present disclosure there is provided a member to form part of an aerosol provision system, wherein the member is configured for releasable attachment to an outer surface of an aerosol provision assembly and defines an aperture through which a control element of the aerosol provision assembly is accessible in use.

BRIEF DESCRIPTION OF THE DRAWINGS

Embodiments of the disclosure will now be described, by way of example only, with reference to the accompanying drawings, in which:

FIG. 1A shows a perspective view of an example aerosol provision system.

FIG. 1B shows a top view of the example aerosol provision system of FIG. 1A.

FIG. 2 shows a front view of an example aerosol provision system comprising a replaceable consumable.

FIG. 16 shows a front view of another example aerosol provision system comprising a first portion recessed with respect to a second portion.

FIG. 17 shows a cross sectional view of the aerosol provision system of FIG. 16.

DETAILED DESCRIPTION

Figure 3:
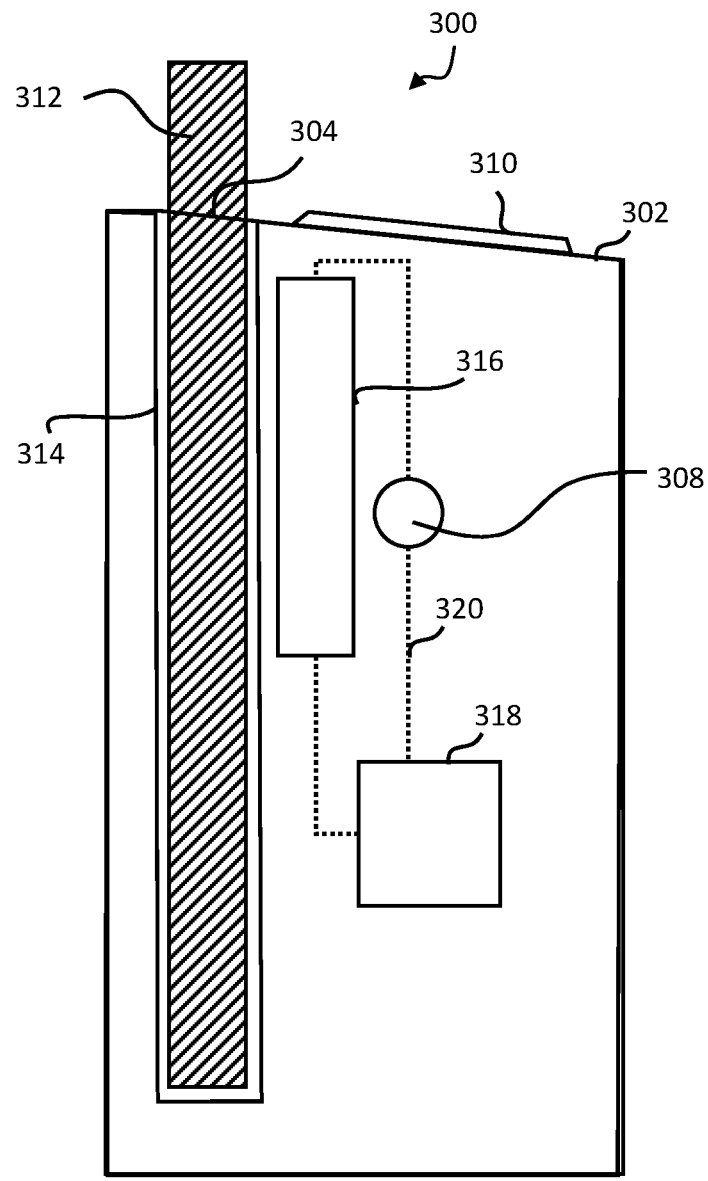
FIG. 3 shows a schematic view of an example aerosol provision system.

In some examples, an aerosol provision system comprises an assembly defining an opening configured to receive a replaceable consumable, and a removable member releasably engaged with the assembly, the removable member configured to form part of an outer surface of the system, and positioned so as not to obstruct the opening.

In some examples, the removable member conforms to, and covers at least part of an outer surface of the assembly. For example, the removable member may have generally the same shape of the part of the outer surface which is covered. The removable member may abut the part of the outer surface which is covered. The removable member may be spaced less than 2 mm, or less than 1 mm from the part of the outer surface which is covered. In some examples there may be substantially no gaps and/or voids between the removable member and the part of the outer surface which is covered across substantially the whole area of the removable member.

By providing an aerosol provision system with a removeable member, components of the assembly may be protected from impact forces. Furthermore, the removable and replaceable nature of the member allows a user to customize the assembly. For example, specific textures, grip, or ergonomics can be provided. The removable member can be releasably engaged with a surface of the assembly to provide protection at specific locations. One or more removable members may be provided for attachment to the assembly to increase protection around the assembly at a plurality of locations. The aerosol provision system may also be an aerosol provision device, or a device or system for generating an inhalable medium. In some examples, the assembly may be an aerosol provision device.

In one example, the aerosol provision system comprises a heater arranged to heat the replaceable consumable in use. Heated products from the replaceable consumable may then be inhaled by a user of the system. In one example, the system comprises a heating device which releases compounds by heating but not burning, a substrate material, such as the replaceable consumable. The material may be for example tobacco or a non-tobacco material, which may or may not contain nicotine. In one example the heating device is a tobacco heating device. In one example a consumable product may be, for example, of a predetermined or specific size that is configured to be placed within a receptacle sized to receive the consumable product. In one example, a replaceable consumable is tubular in nature, and may be known as a "tobacco stick". In some examples the consumable may comprise tobacco formed in a specific shape which is then coated, or wrapped in one or more other materials, such as paper or foil. In one example, the replaceable consumable is received within the opening along an insertion axis. In another example, the replaceable consumable comprises a chamber of liquid, the liquid comprising nicotine. The liquid, upon heating, volatizes and is inhaled by a user of the device.

In examples, the aerosol provision system is portable, for example having no dimension greater than 20 cm, 15 cm or 10 cm.

In some examples the removable member is a removable panel, sized to cover at least a portion of a surface of the assembly.

In an example, at least one of the removable member and the assembly comprises an attachment element to attach the removable member to the assembly. In another example, both the removable member and assembly comprise corresponding attachment elements. These attachment elements provide means to attach and/or secure the removable member to the outer surface of the system.

In one example, the attachment element comprises a magnet. In an example where only one of the removable member and the assembly comprises a magnet, the other of the removable member and the assembly comprises magnetic material, where a magnetic material is a material that is attracted to the magnet. An example magnetic material is steel; however, other magnetic materials may be used.

In another example both the removable member and the assembly comprise at least one magnet. In one arrangement a first magnet provided on the removable member is arranged adjacent to a second magnet of opposite polarity provided on the assembly. This may assist alignment of the removable member with the assembly when the member is attached to the assembly. In another arrangement both the assembly and the removable member comprise at least one magnet and magnetic material, the magnets arranged so that they attach to magnetic material when assembled; this may result in a more secure attachment.

In some examples, the attachment element is configured to be slidably received within a channel. Such a construction may provide a guide path for attaching the removable member. For example, the attachment element may comprise an elongate member, an edge or rail configured to engage a corresponding attachment element such as a channel or groove in a surface of the other of the removable member and the assembly. The channel may define an axis, such that the elongate member is received within the channel by moving the elongate member in a direction parallel to the axis. In some examples the elongate member comprises a lip, rim or flange, to interlock with a correspondingly shaped channel.

In one example, the attachment element is configured to provide a snap-fit connection between the removable member and the assembly. To attach the removable member to the assembly, the removable member may be moved towards the assembly, for example in a direction substantially perpendicular to the surface of the assembly. In one example, the attachment element may comprise an elongate member, an edge or rail configured for engaging a corresponding channel, groove or ridge in a surface of the other of the removable member and the assembly.

The use of elongate attachment elements may provide a greater contact area, and therefore increase friction and attachment security of the removable member to the assembly, whether the attachment is slidably received or snap-fit. In other examples such as those for using a snap-fit connection, the attachment elements are not elongate, and instead comprise any suitably shaped protrusion to be received within a correspondingly shaped aperture.

In some examples one or more magnets may be used in combination with other attachment elements described above.

In one example, the assembly comprises a control element, and the removable member defines an aperture through which the control element is accessible. The control element may be a sensor, such as a capacitive or resistive sensor, a button, or a switch in some examples. Activation of the control element causes the assembly to operate. For example, activation of the control element may cause a heater to turn on to heat the removable consumable. Provision of the aperture allows the removable member to be attached to the assembly without obstructing operation of the assembly after the removable member is attached. In one example, the control element and the aperture are aligned coaxially.

In one example, the control element projects from a surface of the assembly such that the control element is at least partially received within the aperture. The control element may be substantially flush with an outer or external surface of the removable member after assembly, the control element may extend though the aperture and project above an outer or external surface of the removable member, or the control element may have a surface which is recessed below an outer or external surface of the control element. This construction may improve alignment when fitting the removable member to the assembly. In addition, the protruding control element may limit lateral movement of the removable member, meaning it is more securely attached to the assembly.

In one example, the system further comprises a control member disposed between the removable member and the control element, such that operation of the control member operates the control element. In one example the control member is at least partially attached to an inner or internal surface of the removable member. In some examples the control member is at least partially constructed from the same material as the removable member.

In one example, the assembly comprises one or more light sources on, or in proximity to, the control element and the control member comprises transparent, transmissive or translucent material, through which light from the one or more light sources can pass. This allows the light source to be observed once the removable member is attached to the assembly.

In one example a recess is defined by a portion of a surface of the assembly, and the removable member is received within the recess. In one example, the surface of the assembly is an outer surface of a housing. Such a construction may provide a guide for positioning the removable member in place. Furthermore, by receiving the removable member at least partially within the recess, the removable member may be less likely to detach from the assembly.

In one example, a thickness (such as a depth dimension) of the removable member is substantially equal to a depth of the recess. This means that when the removable member is received within the recess, an outer surface of the removable member lies substantially flush with the surface of the assembly. This construction may provide a more ergonomic design that is easier to hold for example.

In one example, at least a portion of an external surface of the removable member comprises a gripping surface. This may provide the system with improved grip, thereby reducing the likelihood of being dropped and damaged. In some examples, the gripping surface may be formed into a pattern, such as a pattern of dots. In some examples, the gripping surface comprises one or more raised portions, such as knurls or dots. In other examples the gripping surface may be roughened or textured. In other examples the gripping surface may have a matt finish with adjacent areas of the system and/or removable member not part of the gripping surface having a glossy finish, a polished finish, or a smooth finish. In other examples, the gripping surface may be formed from a material, such as rubber or a plastics material, with a higher coefficient of friction than the removable member and/or an outer surface of the assembly.

In one example, the removable member is formed from a material different to that of a surface of the assembly. For example, a housing of the assembly and the removable member may be constructed from different materials. This can provide different textures and grip for a user. In one example, the outer surface of the assembly is at least partially constructed from a material which is cheaper than the material of the removable member, which may allow the overall cost of manufacture to be reduced.

In one example, the removable member defines a curved surface, the curved surface being dimensioned, configured or arranged to abut a corresponding curved surface of the assembly. The curved surface may be curved in one, two or three dimensions for example. The curved surface may allow a more ergonomic design that is more comfortable to hold.

In one example, the removable member is constructed from, or comprises metal. For example, the metal may be steel. In some examples the metal is rolled steel.

In some examples the removable member is a first removable member configured to releasably engage with a first surface of the assembly, and the system further comprises a second removable member configured to releasably engage with a second surface of the assembly. By having two or more removable members, protection may be provided to many surfaces of the assembly. The first surface may be a front surface and the second surface may be a back surface, for example.

In some examples, the system may further comprise one or more removable side members, the removable side members configured to releasably engage with a lateral or side surface of the assembly.

In some examples, the outer surface of the assembly comprises a first portion and a second portion, the first portion being recessed with respect to the second portion to provide a fulcrum about which the removable member can rotate. For example, a stepped profile of the outer surface can provide a pivot point, edge or line about which the removable member can pivot. A groove or recess may be provided by the first portion, which is at least partially covered by the removable member when it is attached to the assembly, allowing a user to apply a force to the removable member at a specific location towards one edge to cause the removable member to lift at the opposite edge so that the user can easily remove the removable member from the assembly. For example, an edge at which a force is applied rotates towards the assembly and an opposite edge rotates away from the assembly. This arrangement means the removable member can be removed easily, without the aid of tools for example. In some examples there may be one or more first portions. The one or more first portions are arranged beneath the removable member when it is attached to the assembly, which allows a user to apply a force to one or more regions on the removable member to detach it from the assembly and remove it more easily.

In some examples the first portion comprises one or more sidewalls and a base. However, in other examples the first portion may have a concave or convex form, with a curved base and sidewalls. The sidewalls may be substantially perpendicular to the base or angled with respect to the base.

In some examples the fulcrum is provided by two surfaces joining at an angle of about 90 degrees relative to each other. For example, the sidewall of the first portion may join a top surface of the second portion. In other examples the fulcrum is provided by two surfaces joining at an angle other than 90 degrees, such as less than 90 degrees or greater than 90 degrees but less than 180 degrees. In some examples the fulcrum may be provided by a curved surface, in which case the curved surface may act like a cam to at least some extent. For example, the curved surface may have a smaller radius of curvature than the removable member, in order to provide a fulcrum when the removable member is itself curved.

In some examples the first portion is dimensioned to receive an edge of the removable member as the removable member rotates about the fulcrum such that an opposite edge of the removable member rotates away from the second portion. This allows the removable member to rotate by a desired degree and without obstruction. For example, the first portion may have a defined depth, width and length within which an edge of the removable member can be accommodated as the removable member pivots towards the assembly at this edge. In one example, the length of the first portion may be equal to or greater than a length dimension of the removable member. In another example, the length of the first portion may be equal to or greater than a width dimension of the removable member. The depth of the first portion may limit the angle of rotation of the removable member. The width of the first portion may be sized to allow easy rotation when a force is applied by a user's digit. The width dimension may also affect the angle through which the removable member can rotate.

In some examples the outer surface of the assembly comprises a third portion, the second portion being recessed with respect to the third portion by a depth dimension substantially equal to a thickness dimension of the removable member. In other words, both the first and second portions are recessed with respect to the third portion. The first and second portions may together define a recessed area substantially equal in size to an area of the removable member. This combined recessed area allows the removable member to be received within it, such that an outer surface of the removable member is substantially flush with the third portion of the outer surface of the assembly. The removable member therefore fully or partially covers the first and second portions when attached to the assembly. This can provide the assembly with a level outer surface, which can be more ergonomic and more comfortable to hold.

In some examples the first portion is dimensioned such that the opposite edge of the removable member extends above the third portion as the removable member rotates about the fulcrum. For example, the depth and/or width dimension of the first portion may be appropriately sized to allow the opposite edge of the removable member to lift away from the assembly by a distance so that it protrudes above the third portion of the outer surface. This again allows easier removal because the opposite edge of the removable member can be easily gripped.

In some examples the removable member is attached to the assembly by one or more attachment elements and at least one of the one or more attachment elements is configured to detach as the removable member rotates about the fulcrum. Thus, the force required to detach the attachment element is less than the average leverage force generated by the removable member as it rotates about the fulcrum. The leverage of the removable member can therefore aid detachment of one or more attachment elements, which reduces the effort required for a user to detach the removable member after rotation. For example, the attachment elements located further away from the fulcrum (and therefore closer to the opposite edge of the removable member) may be detached upon rotation.

In some examples the plurality of attachment elements are magnets arranged on the second portion. Magnets are attachment elements that can be detached more easily than some other attachment elements. By being arranged on the second portion, rather than on the removable member itself for example, the weight and cost of the removable member can be reduced.

In some examples, a first magnet is arranged to engage the removable member at a first region, and a second magnet is arranged to engage the removable member at a second region, the second region being:

closer to the opposite edge than the first region; and
closer to a midpoint of a length dimension of the removable member than the first region.

This arrangement of magnets improves usability of the assembly. For example, the action may be considered smoother and less abrupt than other magnet arrangements. Here, "engage the removable member" may mean to directly or indirectly engage the removable member. For example, the removable member may comprise magnetic material which is attracted to the magnets. This is a direct engagement. Alternatively, a collocated magnet may also be present on the removable member so that the magnet on the second portion indirectly engages the removable member, via the collocated magnet.

In some examples the first portion comprises one or more raised sections being raised above a base of the first portion. In other words, the base of the first portion may not be uniformly recessed with respect to the second portion but instead comprise one or more regions which are recessed by a lesser degree, or are not recessed at all. This can be useful when the material beneath the first portion is thin. These raised portions add additional thickness to the material below the recess to provide strength to the assembly. These raised portions may act as a heat sink, and/or help protect components of the assembly which may reside below the first portion. The raised sections may not be recessed with respect to second portion or may be recessed with respect to the second portion.

In some examples the first portion has a width dimension of about 1.5 to about 5.75 mm. In some examples the first portion is recessed with respect to the second portion by a depth dimension of about 0.2 to about 0.4 mm. These dimensions have been found to provide a balance between sufficient rotation to detach the removable member and ease of use.

In one example, the assembly comprises a removable casing, the removable casing forming part of an outer surface of the assembly, and wherein the removable member is configured for releasable engagement with the removable casing. The removable casing may be a cover or sleeve configured to be fitted to a housing forming part of the assembly. The casing therefore covers or surrounds the housing, and may help protect components of the assembly from damage. In this example, the assembly may therefore comprise a housing and the removable casing, where the housing defines the opening configured to receive a replaceable consumable. In such an example, the removable member may therefore be attached to an outer surface of the casing rather than being fitted to the housing. The removable member and/or removable casing may comprise any of the above-mentioned features to allow the removable member to be releasably engaged with the removable casing. In one example, both the removable member and removable sleeve each define an aperture through which a control element is accessible. This combination of removable member and removable cover may further enhance protection of the assembly components.

In another example, the removable member releasably engaged with the assembly is itself a removable casing, and the removable casing defines an opening configured to receive at least a portion of the assembly such that the removable casing covers at least a portion of a surface of the assembly. Therefore, the removable casing may be a cover or sleeve configured to be fitted to the assembly. The casing may help protect components of the assembly, such as a housing, from damage.

In one example, the assembly comprises a control element, and the removable casing defines an aperture through which the control element is accessible.

In one example, at least a portion of an external surface of the removable casing comprises a gripping surface.

In some examples the removable casing defines two open ends. In another example the removable casing defines one open end and comprises a closed end, or a partially closed end. An open end, or partially closed end may allow charging ports, or other components of the assembly to be reached without obstruction.

In some examples the removable casing is formed from a "hard" material, such as polycarbonate, and is capable of withstanding impact damage. In some examples the removable casing is constructed from clear, transparent, transmissive or translucent material to allow features of the assembly to be seen. In other examples, the removable casing is constructed from metal.

In some examples, the system further comprises a strap or lanyard attachable to the removable casing. In some examples the casing defines a through hole, and the strap or lanyard is attachable to the through hole.

According to some examples, a member forms part of an aerosol provision system, wherein the member is configured for releasable attachment to an outer surface of an aerosol provision assembly and defines an aperture through which a control element of the aerosol provision assembly is accessible in use.

In one example, the member comprises at least one of a magnet and magnetic material.

In one example, the member comprises an attachment element for engaging the aerosol provision assembly.

In one example, the attachment element comprises one of:
an elongate member configured for engaging a channel defined by a surface of the aerosol provision assembly; and
a channel defined by a surface of the member, the channel configured for engaging an elongate member formed on a surface of the aerosol provision assembly.

In one example, the elongate member is slidably received within the channel.

In one example, the attachment element is configured to provide a snap-fit connection.

In one example, the aperture is configured to at least partially receive the control element in use.

In one example, the member is configured to be received within a recess defined by a portion of a surface of the aerosol provision assembly.

In one example, the member is a removable casing and defines an opening configured to receive at least a portion of the aerosol provision assembly such that the removable casing covers at least a portion of a surface of the aerosol provision assembly. In one example the removable casing is configured for releasable engagement with a second member, the second member being configured to form part of an outer surface of the aerosol provision system.

In one example, at least a portion of an external surface of the member comprises a gripping surface.

Referring to FIG. 1A, there is shown an example of an aerosol provision system 100. In broad outline, the system 100 may be used to heat a replaceable consumable, to generate an aerosol or other inhalable medium which is inhaled by a user of the system 100. FIG. 1A shows the system 100 without a replaceable consumable. FIG. 2 shows a system 200 with a replaceable consumable 212 inserted into an opening 204.

In FIGS. 1A and 1B, the system 100 of this example comprises an assembly which includes a housing 102. The housing 102, and therefore the assembly, has an opening 104 which is configured to receive a replaceable consumable. In one example, the replaceable consumable comprises tobacco, and the consumable may be partially inserted into the opening 104 so that it is received within the housing 102. In use, a heater (shown in FIG. 3) heats the replaceable consumable. The assembly may also comprise a lid, or cap 110, to cover the opening 104 when no consumable is in place. In FIGS. 1A, 1B and 2, the cap 110, 210 is shown in an open configuration, however the cap 110 may slide into a closed configuration when the consumable is removed.

FIG. 1A depicts a removable member 106 engaged with the assembly. The removable member 106 therefore forms part of an outer surface of the system 100, and is positioned so as not to obstruct the opening 104. In the example of FIGS. 1 and 2, the removable member 106 is panel-like, and is shown attached to the housing 102 of the assembly. In other examples however, the removable member may be attached to other parts of the assembly. The removable member 106 is releasably attached with the assembly such that it can be removed, and replaced by another removable member 106.

The provision of a removable member 106 may allow components of the assembly to be protected from impact damage. Different colored, textured, or patterned removable members 106 may be fitted to the assembly as the user desires.

The removable member 106 may be constructed from any suitable material. In the examples of FIG. 1A, the removable member 106 is constructed from metal, such as steel or aluminum. In one example the removable member 106 is constructed from rolled steel. In other examples the removable member is constructed from a plastics material.

The system 100 further comprises a control element 108 as part of the assembly. The control element 108 in this example is a button or a switch, and when a user activates the control element 108, a heater is switched on. Activating the heater causes the replaceable consumable to be heated such that an aerosol is generated. In FIG. 1A, the removable member 106 defines an aperture 122 through which the control element 108 is accessible, for example the removable member 106 comprises a circular cut-out that allows the control element 108 to be accessed.

FIG. 2 shows an aerosol provision system 200 with a replaceable consumable 212 inserted. In this example, the replaceable consumable 212 comprises tobacco, and is partially inserted into the opening 204 so that it is received within the housing 202. The system 200 comprises features substantially the same as those described in relation to FIGS. 1A and 1B.

Referring now to FIG. 3, there is shown a schematic of an example aerosol provision assembly 300. The assembly 300 comprises a heater 316 arranged to heat the replaceable consumable 312 once the replaceable consumable 312 has been at least partially inserted into the opening 304 and received within a chamber or receptacle 314. In this example, the heater 316 is powered by a battery 318 and is electrically connected to the battery 318 via one or more wires 320, shown depicted as dashed lines. Also connected to the battery 318 and the heater 316 is the control element 308, which is operated by a user to control the energy supply to the heater 316. The heater 316 may be an electrically resistive heater, including for example a nichrome resistive heater, a ceramic heater, etc. The heater 316 may be an induction heater. Other heating arrangements may be used, including non-electrical heating arrangements.

Figure 4:
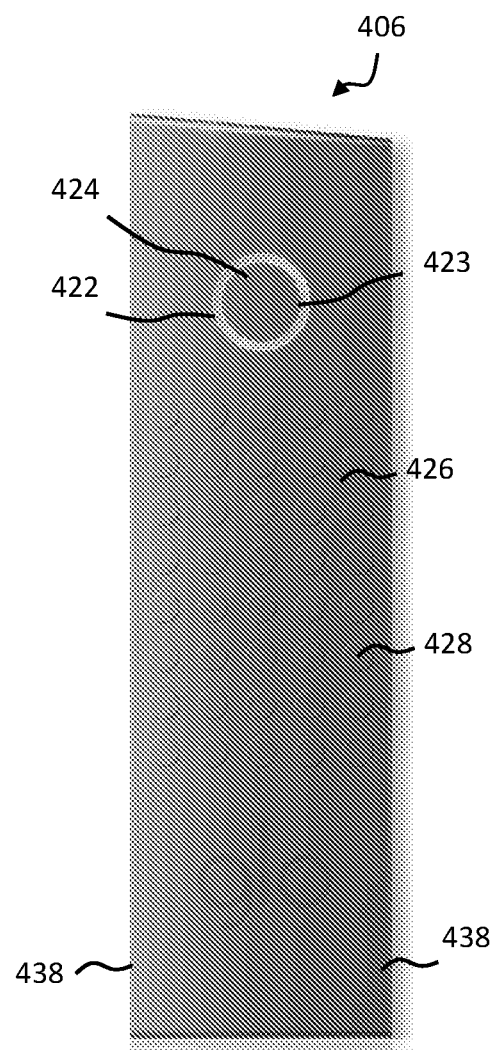
FIG. 4 shows an example removable member.

Referring now to FIG. 4, there is shown an example removable member 406. In this example the removable member 406 is shown separated and therefore removed from the assembly. The removable member 406 may be releasably engaged with a surface of the assembly. The removable member 406 therefore is sized to cover at least a portion of an outer surface of the assembly. In this example the removable member 406 defines a curved surface to abut a corresponding curved surface of the assembly. In other examples the removable member 406 is substantially flat, or planar. In either case, the removable member is configured to conform to and cover at least part of an outer surface of the assembly. For example, once the removable member is attached to the assembly, an inner surface of the removable member abuts the outer surface of the assembly to which it is attached. In one example, the inner surface of the removable member lies against the outer surface of the assembly, such that substantially the spacing between the two surfaces is minimal. In one example, the removable member 406 is formed with contours to correspond to the contours of the outer surface of assembly below.

In the example of FIG. 4, the removable member 406 is provided with a gripping surface 426 on its exterior. The gripping surface improves the grip when held by a user. In FIG. 4, the gripping surface includes one or more raised portions that project from the gripping surface. The raised portions may include dots 428 as shown in FIG. 4, or ridges, or contours that protrude from the surface of the removable member 406. In some examples the raised portions are integral to the surface of the removable member, however in other examples these portions may be adhered to the surface of the member. The gripping surface may comprise rubber, for example.

In one example, the removable member 406 defines an aperture 422 through which the control element of the assembly is accessible. In this example, the removable member 406 further comprises a control member 424. The control member 424, in effect, provides an extension of the control member, such that operation of the control member 424 operates the control element below. The control member may cover the control element, and therefore provide protection. In other examples the control member 424 is not included.

The control member 424 may be disposed between the removable member 406 and the control element, and may be positioned within the aperture 422. In some examples the control member 424 is at least partially attached to an inner surface of the removable member 406. In this example, the control member is at least partially constructed from the same material as the removable member 406.

In one example, the assembly may comprise one or more light sources on, or in proximity to, the control element. The control member 424 may therefore comprise transparent or translucent material 423, through which light from the one or more light sources can pass. This allows the light source to be observed once the removable member 406 is attached to the assembly.

Figure 5:
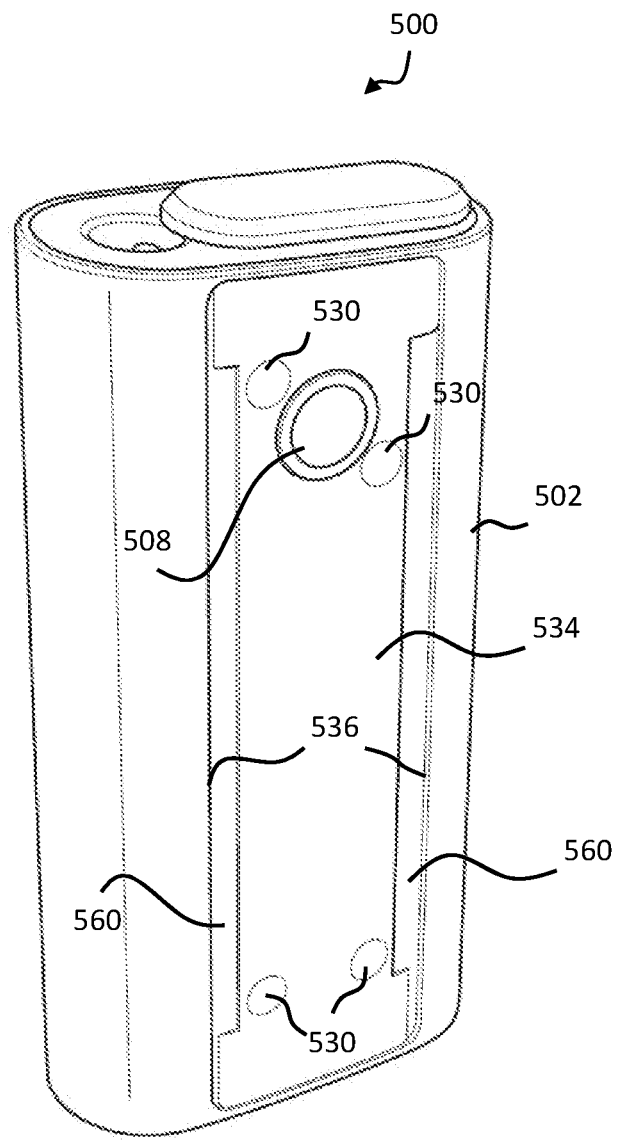
FIG. 5 shows a perspective view of a housing comprising a magnet in accordance with an example.

FIG. 5 depicts part of an example assembly 500 configured to receive, and engage with a removable member. In this example a housing 502 of the assembly 500 comprises one or more attachment elements to attach the removable member to the assembly. Attachment elements include any features that provide means of attachment. For example, in the example of FIG. 5, the attachment elements comprise magnets 530. Although four magnets are shown here, it will be appreciated that one or more magnets may be suitable to hold the removable member in place. To attach the removable member to the assembly, the removable member may comprise magnetic material, such as steel, that experiences an attractive force when in proximity to the magnets on the housing 502. In another example, the removable member may also comprise one or more corresponding magnets, in addition to, or instead of comprising magnetic material. For example, the removable member may comprise four magnets arranged on the surface of the removable member to engage the four corresponding magnets on the housing 502.

In the example of FIG. 5, the magnets are adhered to the surface of the assembly 500 using adhesive, such as epoxy. In other examples however, the magnets may be partially or fully embedded in the surface of the assembly.

In the example of FIG. 5, the control element 508 is arranged on the housing 502. However, in other examples, the assembly 500 defines an aperture through which a control element may be accessed. The control element therefore may be arranged within the assembly 500 on an element separate to the housing 502. In either case, the control element may project from a surface of the assembly such that the control element 508 is at least partially received within an aperture of the removable member.

In the example of FIG. 5, a recess 534 is defined by a portion of a surface of the assembly, and the removable member is received within the recess 534. For example, a portion of an outer surface of the housing 502 may be recessed with respect to the rest of the outer surface of the housing 502. A substantially rectangular recess 534 is shown across the surface of the housing 502 in FIG. 5, however other shaped recesses may be provided. The recess 534 allows the removable member to be at least partially received within the recess 534. In other examples however, there is no recess.

In some examples the recess comprises sidewalls 536, which are parallel to each other. In other examples, the sidewalls may not be parallel. The removable member may comprise corresponding side edges 438 (shown depicted in FIG. 4), such that as the removable member is attached to the assembly 500 and received within the recess 534, the sidewalls 536 of the recess 534 are configured to abut the side edges 438 of the removable member. In one example, the sidewalls 536 have a height dimension that is substantially equal to a height dimension of the side edges 438 (and/or a thickness of the removable member), such that an outer surface of the removable member lies flush with the surface of the assembly.

Regardless of whether the assembly defines a recess or not, the removable member is configured to conform to, and cover at least a portion of the outer surface of the assembly. In other words, the removable member is shaped to fit and cover the surface of the assembly below. In some examples, the shape of the removable member conforms to the shape of the assembly surface with which the removable member is engaged. In some examples, although the surface of the assembly is recessed, the side edges of the removable member are to be received within the recess. In other words, in some examples, the removable member does not extend across the recess and define a cavity in combination with the surface of the housing.

Figure 6A:
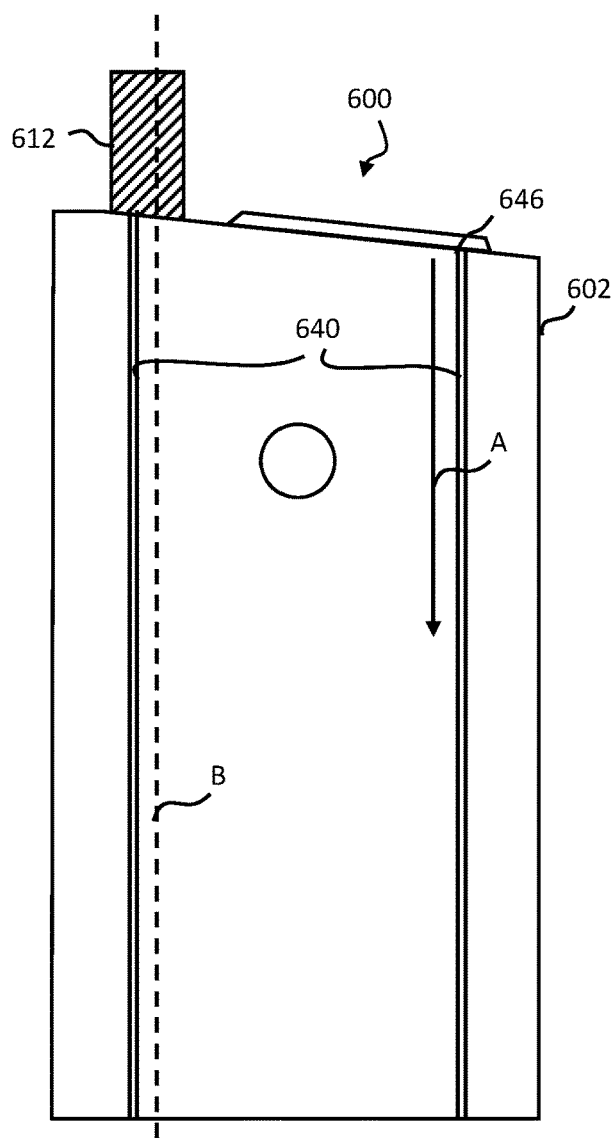
FIG. 6A shows a front view of attachment elements on an example aerosol provision assembly.
Figure 6B:
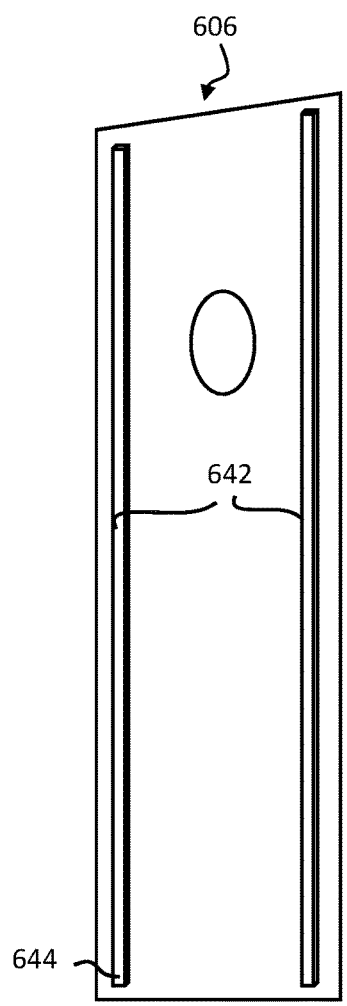
FIG. 6B shows a perspective view of attachment elements on an example removable member.

FIG. 6A shows a schematic of another example aerosol provision assembly 600. FIG. 6A depicts a front view of the assembly 600 comprising a housing 602, where the housing 602 is configured to receive, and engage with the removable member 606 depicted in FIG. 6B. FIG. 6B depicts the removable member 606 in perspective to aid understanding of the attachment elements, described below.

FIGS. 6A and 6B show one or more attachment elements to attach the removable member 606 to the assembly 600. In this example, attachment elements are provided on the assembly 600 and corresponding attachment elements are provided on the removable member 606. An example attachment element and a corresponding attachment element includes a protrusion 642 formed on one surface and a corresponding aperture 640 formed on another surface. The protrusion 642 is configured for engaging the aperture 640. When the protrusion is releasably received in the aperture, the connection elements together provide means for securing the removable member 606 to the assembly 600. The protrusion and aperture may together provide a friction fit, interlock or otherwise engage to hold the removable member 606 in place. One or more magnets may also be used in combination with these attachment elements.

In the example of FIGS. 6A and 6B, two attachment elements are provided on the housing 602 of the assembly 600, and these attachment elements comprise channels 640. Two corresponding attachment elements are provided on the removable member 606, and these attachment elements comprise elongate members 642. It will be appreciated however that the elongate members 642 may alternatively be provided on the assembly 600, and the channels 640 may be provided on the removable member 606. In addition, as mentioned above, although the protrusions 642 and apertures 640 are elongate, any shaped protrusion or aperture may be provided.

Using the attachment elements, the removable member 606 can be affixed to the assembly 600 according to a number of different methods.

According to a first example, to receive the elongate members 642 in the channels 640, the removable member 606 may be placed in proximity to the assembly 600 and the elongate members may be slidably received within the channels. For example, bottom edges 644 of the attachment element 642 may be inserted into top ends 646 of the channels 640 and moved in a direction illustrated by arrow A. Frictional forces between the elongate member and the channel help secure the removable member 606 in place. In some examples the elongate members 642 comprise a lip, rim or flange, to interlock or engage with a correspondingly shaped channel 640.

According to a second example, to receive the elongate members 642 in the channels 640, the removable member 606 may be placed in proximity to the assembly 600 and the elongate members may be directly received within the channels. For example, the removable member 606 may be moved towards the assembly, in a direction illustrated by arrow C (shown in FIG. 6C). In one example the attachment element is configured to provide a snap-fit connection between the removable member 606 and the assembly 600. Frictional forces, interlocking and/or engagement between the elongate member and the channel help secure the removable member 606 in place.

In the example of FIGS. 6A and 6B, two attachment elements are shown on each of the assembly 600 and the removable member 606. It will be appreciated that in other examples, any number of attachment elements may be provided on the assembly and the removable member. In some examples, only one of the assembly or the removable member may comprise one or more attachment elements, for example, only one of the assembly or the removable member may comprise one or more magnets.

In the examples of FIGS. 6A and 6B, the channels are arranged parallel to each other, and are also arranged parallel to an insertion axis B, where the insertion axis is defined by the replaceable consumable 612 which is received in the opening in a direction along an insertion axis.

Figure 6C:
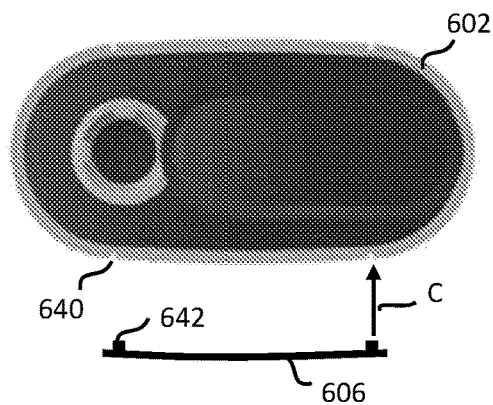
FIG. 6C shows a top view of the example aerosol provision system of FIGS. 6A and 6B.

FIG. 6C depicts a top view of the example aerosol provision system of FIGS. 6A and 6B. Here, the channels 640 can be seen defined by a surface of the assembly 600. In the example of FIG. 6C, the removable member 606 is shown being pressed towards the assembly 600 to affix the removable member 606 to the assembly 600.

Figure 7:
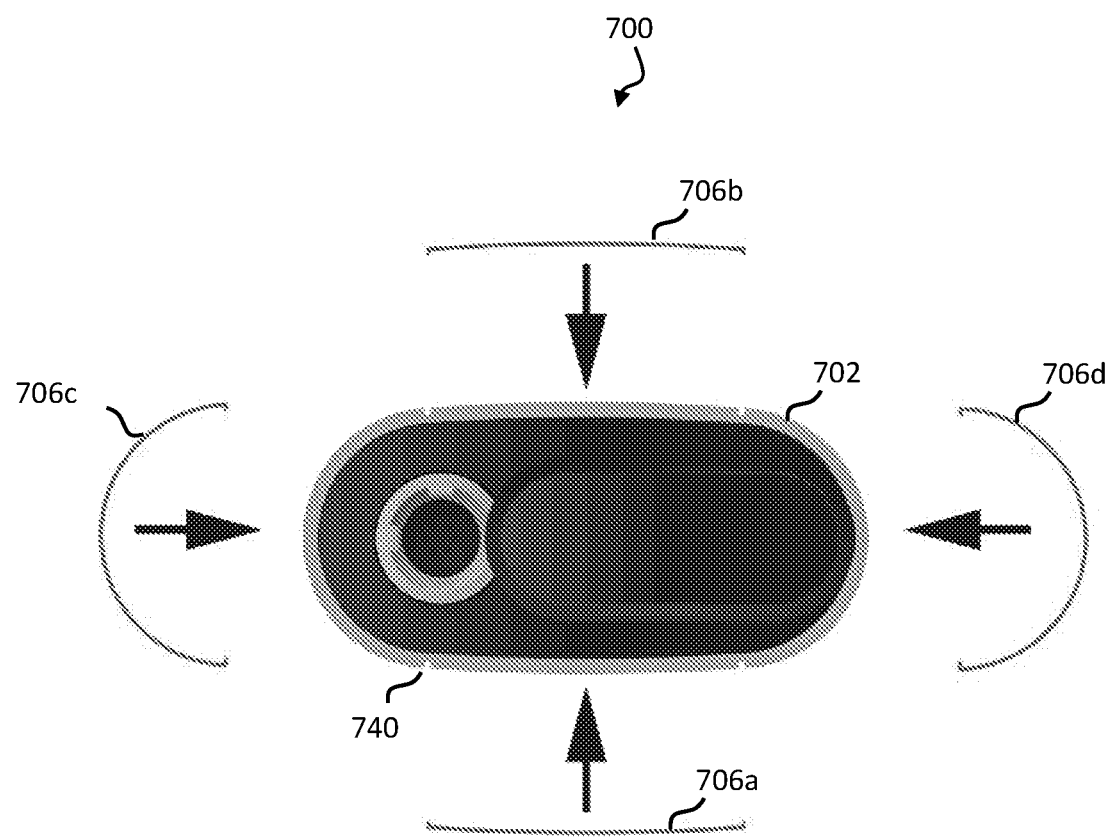
FIG. 7 shows a top view of an example aerosol provision system comprising a plurality of removable members.

As described above, an aerosol provision assembly is configured to receive a single removable member. However, in some examples, the assembly may be configured to receive two or more removable members. FIG. 7 for example, shows a top view of an aerosol provision system 700 comprising a plurality of removable members that may be releasably engaged with the assembly, such as the housing 702.

In the example of FIG. 7, four removable members 706 are shown, however it will be appreciated that fewer or more removable members 706 may be provided. The provision of a plurality of removable members 706 allows different surfaces of the assembly to be protected. In this example system 700, a first removable member 706a is configured to releasably engage with a first surface, such as a front surface, of the assembly, and a second removable member 706b is configured to releasably engage with a second surface, such as a back surface, of the assembly. The system 700 may further comprise a first removable side member 706c and a second removable side member 706d, where the removable side members 706c, 706d are configured to releasably engage with side surfaces of the assembly. In some examples, only some of the removable members 706 define apertures.

The assembly and the removable side members 706 may be provided with any number of appropriate attachment elements described above in relation to FIGS. 5 and 6A-C to attach the removable members 706 to the housing 702. In one specific example, the channels 740 may be wide enough to accommodate two elongate members; one from the first removable member 706a, and one from the first removable side member 706c. However, it will be appreciated that two separate channels may be provided. Although the arrows in FIG. 7 show the removable members 706 being moved towards the assembly, the removable members may also be slidably attached to the assembly.

Figure 8:
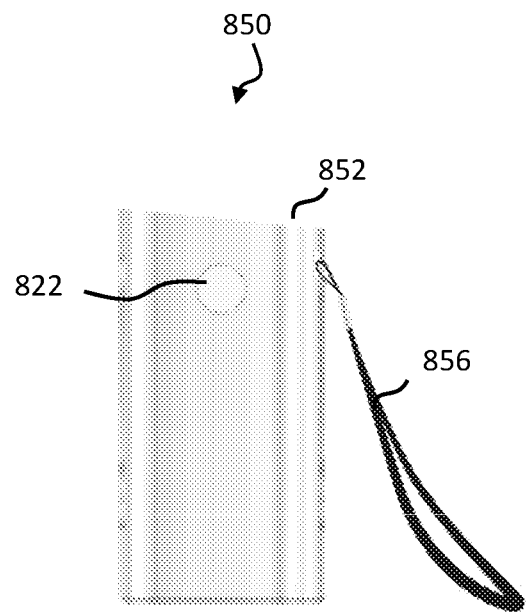
FIG. 8 shows another example removable member.
Figure 9:
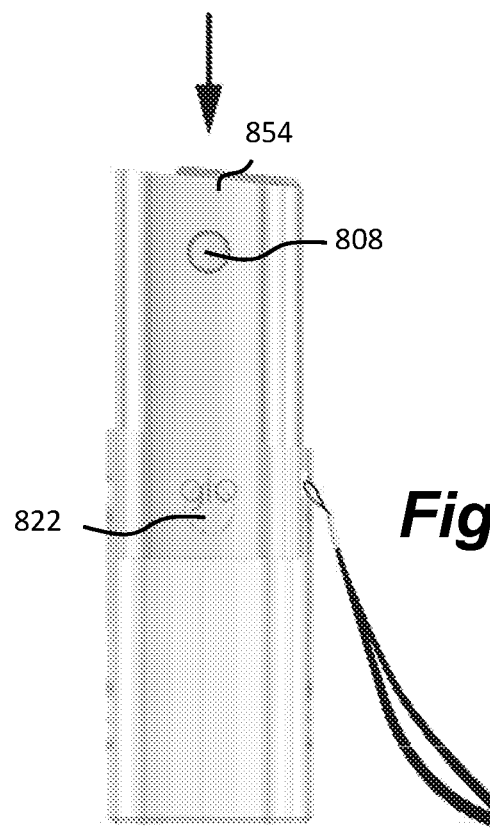
FIG. 9 shows the example removable member of FIG. 8 receiving an example aerosol provision system.

In the examples described above, the removable member has been depicted as panel-like in form, for example, it does not surround an entire outer perimeter of the assembly. However, in some examples the removable member may be a removable casing. FIG. 8 shows an example removable casing/sleeve 800. The removable casing 800 defines an opening 852 configured to receive at least a portion of an aerosol provision assembly, such that the removable casing 850 covers at least a portion of a surface of the assembly. FIG. 9 shows an example aerosol provision assembly 854 being inserted into the removable casing 850 such that the casing 850 surrounds at least a portion of the assembly 854, and in this example the casing surrounds a perimeter of the assembly 854.

In the example of FIG. 9, the assembly 854 comprises a control element 808, and the removable casing 850 defines an aperture 822 through which the control element 808 is accessible. In some examples, the casing 850 does not define an aperture, but instead defines a deformable region that at least partially covers the control element 808 to allow the control element 808 to be operated. The deformable region may be made of material that can be deformed for example. The deformable region may be constructed from the same material as the rest of the casing 850, but the material in this region is comparatively thinner to allow the region to be deformed.

In the example of FIGS. 8 and 9, the removable casing 850 comprises a strap or lanyard 856 attachable to the removable casing 850.

In some examples, at least a portion of the removable casing comprises a gripping surface (not shown). The gripping surface improves the grip when held by a user. The gripping surface may include one or more raised portions that project from the gripping surface. The raised portions may include dots, like those depicted in FIG. 4, or ridges, or contours that protrude from the surface of the removable casing 850.

The casing 850 may be formed from a substantially hard material that maintains its shape. The casing 850 may be formed with contours to correspond to the contours formed by features of the assembly 854. The casing 850 may be constructed from plastic or metal in some examples. In the example of FIGS. 8 and 9, the casing 850 is constructed from clear polycarbonate.

In some examples, an optional removable member like that depicted in FIG. 4 may be attached to the removable casing 850, rather than being attached to a housing of the assembly 854. The removable casing 850, once fitted to the housing, may therefore be said to be part of the assembly, and to form part of an outer surface of the assembly. For example, the assembly may comprise a housing and the removable casing 850. A removable member can therefore be releasably engaged with the assembly by being releasably attached to the removable casing 850. The removable member would therefore form part of an outer surface of the system.

Such a removable member may comprise any or all of the features described in relation to FIGS. 1-7 to allow the removable member to be attached to an exterior surface of the removable casing 850. In addition, the removable casing 850 may comprise any or all of the features described in relation to FIGS. 1-7 to allow the removable casing to receive the removable member. For example, the removable casing 850 may comprise one or more attachment elements, such as channels, elongate members, or magnets to engage with corresponding attachment elements on the removable member. The removable casing 850 may also comprise a recess to receive the removable member. In some examples both the removable casing 850 and the removable member define an aperture through which the control element is accessible. In some examples the control element projects from a surface of the assembly such that the control element is at least partially received within at least one of the apertures defined by the removable member and removable casing.

FIGS. 1-9 and the accompanying description have depicted and described various features to allow a removable member to be attached to an assembly. Features depicted in FIGS. 10-19 will now be described which may assist removal of the removable member from the assembly.

Figure 10:
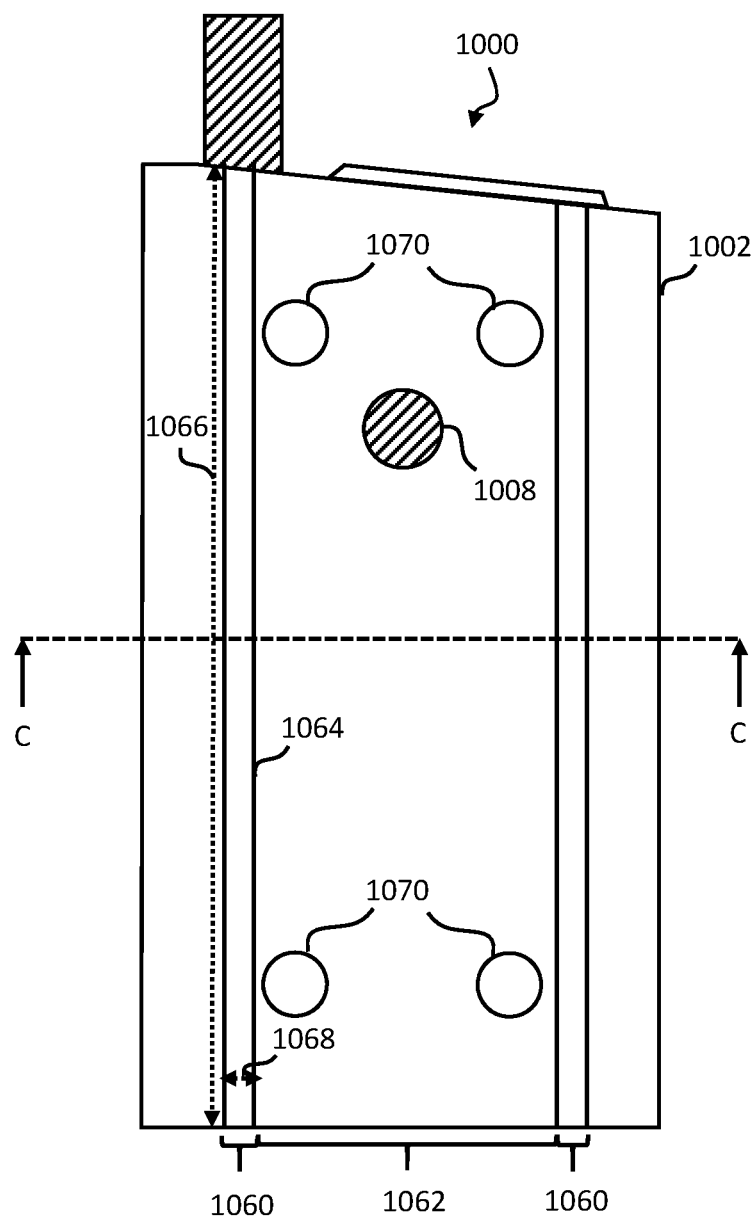
FIG. 10 shows a front view of an example aerosol provision system comprising a first portion recessed with respect to a second portion.

FIG. 10 depicts a system 1000 comprising an assembly without a removable member attached thereto. The housing 1002, and therefore the assembly, comprises an outer surface configured to receive a removable member. In the example depicted, the outer surface of the assembly comprises at least a first portion 1060 and a second portion 1062. The first portion 1060 is recessed with respect to the second portion so that the outer surface of the assembly may have a stepped profile. This stepped profile provides a fulcrum 1064, or pivot point, line or edge, about which the removable member can rotate. The first portion 1060 may have a defined length 1066, width 1068, and depth. The first portion may therefore form a recess or groove in the outer surface of the assembly. In the example of FIG. 10, there are two recessed portions 1060; however, in other examples there may be only one recessed portion, or more than two. Similarly, in the example, the first portion 1060 extends parallel to a longitudinal axis defined by the assembly, but in other examples the first portion 1060 may be arranged at any angle with respect to the longitudinal axis.

A removable member may be attached to the outer surface of the assembly via one or more attachment elements as previously described. In this example, one or more magnets 1070 are arranged on the second portion 1062 of the assembly. Other attachment elements may alternatively be used, such as press-studs or hook and loop fasteners, for example.

When in place, the removable member may at least partially cover the first portion(s) 1060 and the second portion 1062 of the assembly. For example, the removable member may extend between the two recessed portions 1060. The first portions 1060 may therefore be positioned below parallel edges of the removable member when the removable member is in place on the assembly.

In this example, the recess of the first portion 1060 is substantially rectangular in shape; however, other shaped recesses may be provided.

FIGS. 11-14 depict a cross section of the system 1000 taken through the line C-C of FIG. 10 with a removable member 1006 at various positions with respect to the assembly as an example to assist understanding how the first portion can assist removal of the removable member when it is attached to the assembly.

Figure 11:
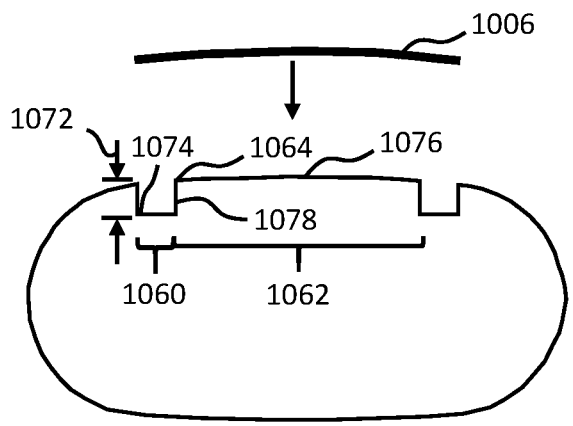
FIG. 11 shows a cross sectional view of the aerosol provision system of FIG. 10, further comprising a removable member being attached to the assembly.

As shown in FIG. 11, the first portion 1060 has a depth dimension 1072, which is defined as a distance between a base 1074, or deepest part of the first portion and a surface 1076 defined by the second portion 1062. The first portion 1060 also comprises one or more side walls 1078 which extend between the base 1060 and the surface 1076 defined by the second portion 1062. The first portion 1060 is therefore recessed with respect to the second portion 1062 to provide a fulcrum 1064. A removable member 1006 can be fitted to the assembly to cover the first portion 1060, the second portion 1062 and therefore the fulcrum 1064.

The example shown also comprises another recessed portion which has the same or similar features corresponding to those described for the first portion 1060. In some examples this other recessed portion is omitted. As will become apparent, the assembly need only comprise one recessed first portion to allow the removable member to be removed.

Figure 12:
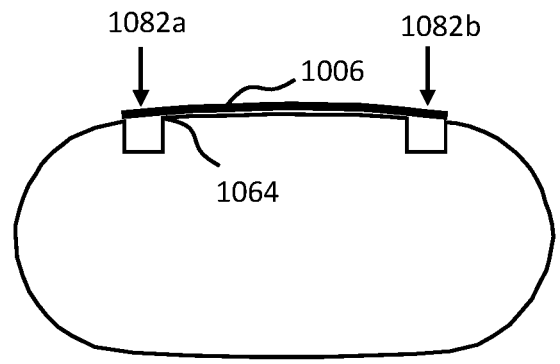
FIG. 12 shows a cross sectional view of the aerosol provision system of FIG. 10, further comprising a removable member attached thereon.

FIG. 12 shows the assembly after the removable member 1006 has been attached via one or more attachment elements. In this example the removable member 1006 defines a curved surface and is configured to engage a similarly curved surface 1076 defined by the second portion 1062. In other examples the removable member 1006 and second portion 1062 are not curved.

To remove the removable member 1006, a user can apply a force at location 1082a or 1082b on the removable member 1006. These locations are located above a respective recessed first portion. For example location 1082a is above first portion 1060. The action of applying a force at location 1082a will be described, but it will be appreciated that a mirror image rotation action occurs for location 1082b.

Figure 13:
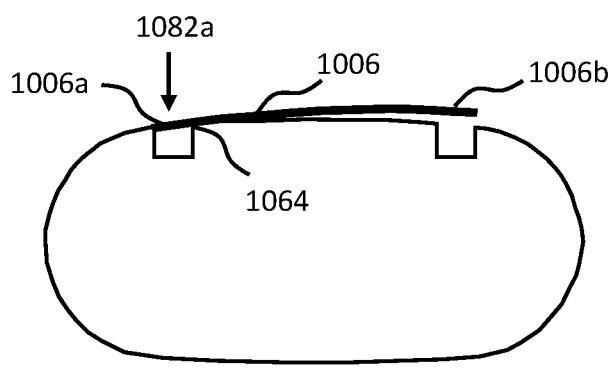
FIG. 13 shows a cross sectional view of the aerosol provision system of FIG. 10, further comprising a removable member being rotated about a fulcrum.

FIG. 13 depicts an initial rotation of the removable member 1006 about the fulcrum 1064 as a user applies a force to location 1082a. The location 1082a is towards an edge 1006a of the removable member 1006. As the force is applied, the removable member 1006 begins to pivot or rotate above the fulcrum 1064 and a region towards an opposite edge 1006b of the removable member 1006 rotates away from the assembly (such as away from the second portion 1062 and/or another recessed portion). The edge 1006a rotates towards the assembly and into the recess provided by the first portion 1060. Hence, during rotation, the edge 1006a of the removable member 1006 is received within the first portion 1060.

Figure 14:
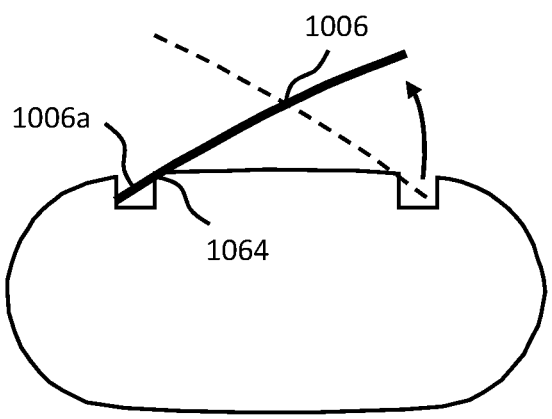
FIG. 14 shows a cross sectional view of the aerosol provision system of FIG. 10, further comprising a removable member at a position of maximum rotation.

FIG. 14 depicts the removable member 1006 at the position of maximum rotation. In some configurations, the position of maximum rotation may occur when the edge 1006a engages the base 1072 of the first portion 1060. At this point, or at any intermediate rotational position, a user can remove the removable member 1006 from the assembly by taking hold of the removable member 1006 and drawing it away from the assembly. For example, the user may insert a digit between the underside of the removable member 1006 and the second portion 1062.

As the removable member rotates, one or more of the attachment elements 1070 may detach. For example, those located further away from the fulcrum 1064 (i.e. those located closer to the opposite edge 1006b of the removable member 1006) may detach as the opposite edge 1006b of the removable member 1006 rotates away from the assembly.

Attachment elements located closer to the fulcrum 1064 may remain attached, for example depending on the degree of separation and rigidity of the removable member 1006.

The dashed line in FIG. 14 depicts the position of maximum rotation of the removable member 1006 if the user had applied a force at location 1082b, rather than at location 1082a. By having multiple fulcrums, the usability of the assembly is increased because the user is provided with a number of different locations at which they can apply a force. For example, to allow removal using either a user's left hand or right hand.

Figure 15:
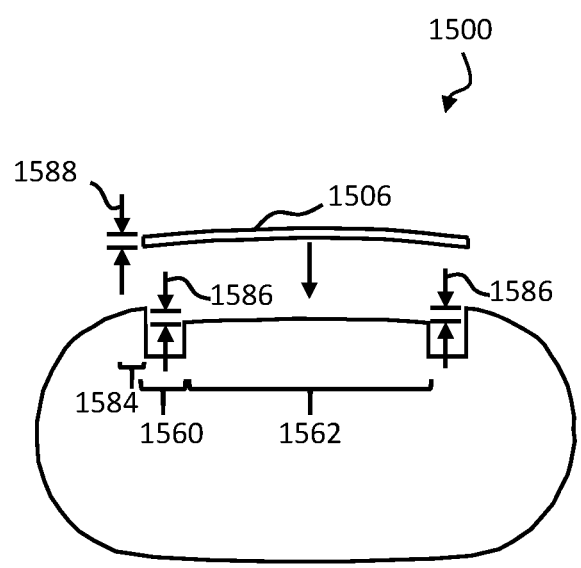
FIG. 15 shows a cross sectional view of another aerosol provision system, comprising a first portion and second portion being recessed with respect to a third portion.

FIG. 15 depicts a cross section of another example system 1500. The example is similar to that shown in FIGS. 11-14; however, in this example the outer surface of the assembly comprises a first portion 1560, a second portion 1562 and third portion 1584, where the second portion 1562 is recessed with respect to the third portion 1584 by a depth dimension 1586 which is substantially equal to a thickness dimension 1588 of the removable member 1506. Accordingly, both the first portion 1560 and the second portion 1562 are recessed with respect to the third portion 1585. The removable member 1506 can be fitted to the assembly to cover the first portion 1560 and the second portion 1562 while remaining flush with third portion 1585. The outer profile of the assembly may therefore be continuous, at least in the region where the removable member 1506 is attached. This can reduce the likelihood of the removable member being accidentally detached during normal use.

FIG. 16 depicts another system 1600 comprising an assembly without a removable member attached thereto. This example differs from those previously described in that the recess or groove is arranged perpendicular to a longitudinal axis defined by the assembly, rather than parallel to the longitudinal axis. The outer surface of the assembly 1602 comprises at least a first portion 1660 and a second portion 1662. The first portion 1660 is recessed with respect to the second portion so that the outer surface of the assembly may have a stepped profile. This stepped profile provides a fulcrum 1664, or pivot point, about which the removable member can rotate. The first portion 1660 may have a defined length 1666, width 1668, and depth. In the example of FIG. 16, there is one recessed portion 1660; however, in other examples there may be two or more recessed portions. For example, there may be a similar recess arranged across the top of the assembly and/or one or more additional recesses like those depicted in FIGS. 10-15.

FIG. 17 depicts a cross section of the system 1600 taken through the line D-D of FIG. 16, with the addition of a removable member 1606 fitted thereto. As shown in FIG. 17, the first portion 1660 has a depth dimension 1672. The first portion 1660 also comprises one or more side walls which extend between the base and a surface defined by the second portion 1662. The first portion 1660 is therefore recessed with respect to the second portion 1662, to provide the fulcrum 1664. A removable member 1606 is also shown fitted to the assembly to cover the first portion 1660, the second portion 1662 and therefore the fulcrum 1664.

FIG. 17 shows the assembly with the removable member 1606 attached via one or more attachment elements, which in this example are magnets 1670. The magnets may be attached to the second portion 1662 or be partially or fully embedded within the second portion 1662.

To remove the removable member 1606, a user can apply a force at a location 1682 towards an edge 1606a of the removable member 1006. Applying a force in this location 1682 will cause an opposite end 1606b of the removable member 1606 to rotate away from the second portion 1662 in the direction of arrow 1680. The edge 1606a rotates towards the assembly and into the recess provided by the first portion 1660. Hence, during rotation, the edge 1606a of the removable member 1606 is received within the first portion 1660.

As the removable member rotates, one or more of the attachment elements 1670 may detach from the removable member. For example, the top magnets 1670 may detach as the opposite edge 1606b of the removable member 1606 rotates away from the assembly.

Figure 18:
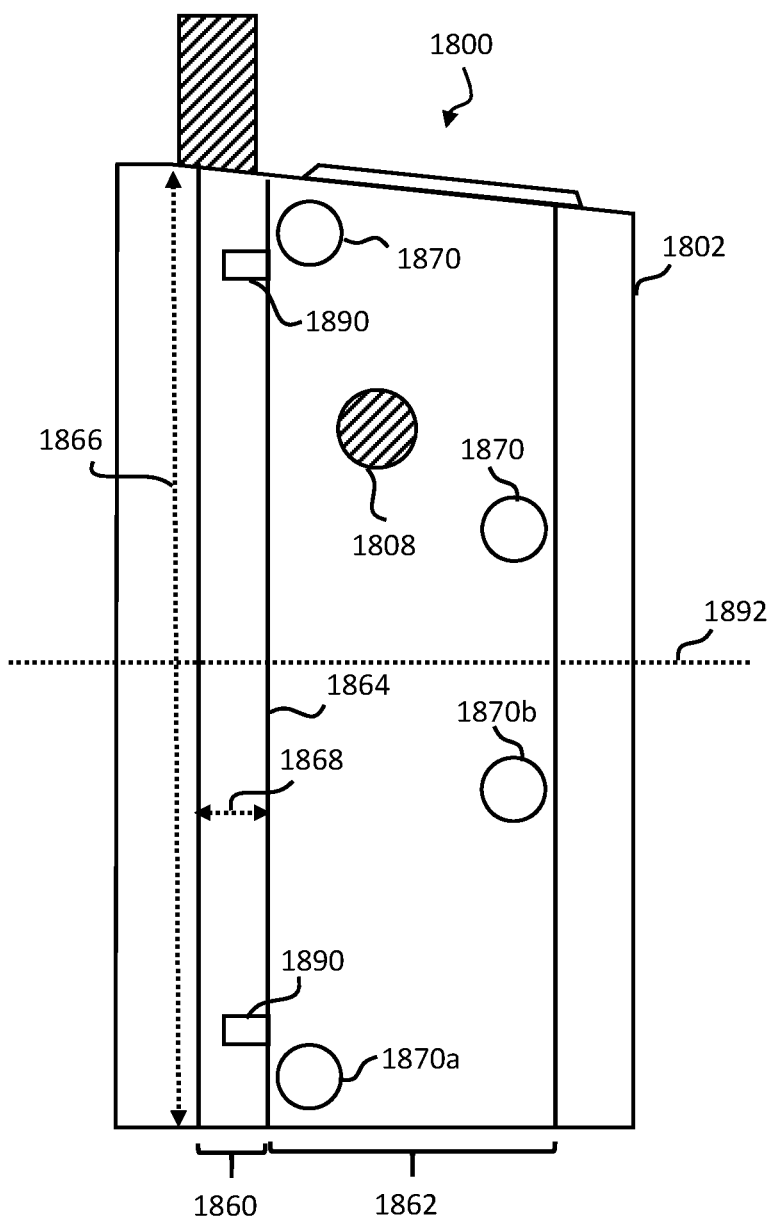
FIG. 18 shows a front view of another example aerosol provision system comprising a first portion recessed with respect to a second portion and one or more raised portions located within the first portion.

FIG. 18 depicts another system 1800 comprising an assembly without a removable member attached thereto. In this example there is a single recessed portion 1860 that is wider than that depicted in FIGS. 10-15. Furthermore, the first portion 1860 comprises one or more raised portions 1890 and a different arrangement of attachment elements 1870.

In this example, the outer surface of the assembly 1802 comprises at least a first portion 1860 and a second portion 1862. The first portion 1860 is recessed with respect to the second portion 1862 so that the outer surface of the assembly may have a stepped profile. This stepped profile provides a fulcrum 1864, or pivot point, about which the removable member can rotate. In the example of FIG. 18, there is one recessed portion 1860; however, in other examples there may be two or more recessed portions. For example, there may be recesses arranged across the top and/or bottom of the assembly and/or one or more additional recesses like those described above with reference to FIGS. 10-15.

The first portion 1860 may have a defined length 1866, width 1868, and depth. The width 1868 is greater than that depicted in FIGS. 1-15. The wider width can be selected to provide a larger area across which a user may apply a force to cause the removable member to rotate and/or allow a greater moment to be applied to the removable member so that removal may be achieved with a lower applied force. A wider width can also be selected to control the angle of rotation of the opposite edge of the removable member. For example, a narrow width may cause the removable member to rotate further away from the apparatus than a wider width of the same depth. A relatively small movement may be more controllable, for example.

In some examples, space within the assembly can be limited. Thus, forming a groove or recess within the outer surface to create the first portion can mean that the material below the groove becomes thin in some sections, such as less than 1 mm or less than 0.5 mm thick, for example. For example, in some sections below the surface, components of the device may extend closer to the outer surface than in other sections. A resulting thin layer of material may reduce structural support of the apparatus, reducing rigidity and potentially increasing the likelihood of damage to components. For example, a thin layer of material can be broken or rupture. Furthermore, if the outer layer is also providing heat insulation, such as to insulate a heater section, a thin layer of material provides little heat insulation.

In the example of FIG. 18, the first portion 1860 comprises one or more raised sections 1890 being raised above a base of the first portion 1860. These are located in regions where the material below would otherwise be considered too thin, for example less than 1 mm or less than 0.5 mm thick due the requirement for internal components to be positioned within the assembly. Accordingly, the depth of the first portion 1860 may be non-uniform. The one or more raised sections 1890 ensure that the material located between the interior and exterior of the device is sufficiently thick to provide structural support, rigidity and/or heat insulation during use. The presence of these one or more raised sections 1890 do not unduly affect rotation of the removable member about the fulcrum 1864.

In some examples, the attachment elements 1870 may be arranged to provide a particular "feel" to the user when the removable member rotates, such as a softer or more abrupt rotation. For example, the distance between the fulcrum and the attachment elements 1870 can alter the force required to cause the removable member to rotate. The arrangement of attachment elements 1870 can also affect the uniformity of rotation. For example, non-symmetric arrangements of attachment elements 1870 can cause the removable member to bend undesirably as a user applies a force to a particular location along the removable member.

One possible arrangement of attachment elements 1870 is depicted in FIG. 18. Four magnets 1870 are arranged on the second portion 1862 and are arranged substantially symmetrically about a midpoint 1892. This midpoint 1892 may coincide with a midpoint of a length dimension of the removable member when it is attached to the assembly. In this particular arrangement, a first magnet 1870a is arranged to engage a first region of the removable member, and a second magnet 1870b is arranged to engage a second region of the removable member. The second region is closer to the opposite edge of the removable member than the first region, and is closer to a midpoint of a length dimension of the removable member than the first region. In other words, the second magnet 1870b is arranged further away from the fulcrum 1864 than the first magnet 1870a, and closer to the midpoint of a length dimension of the second portion 1862. Third and fourth magnets may be similarly arranged.

Figure 19:
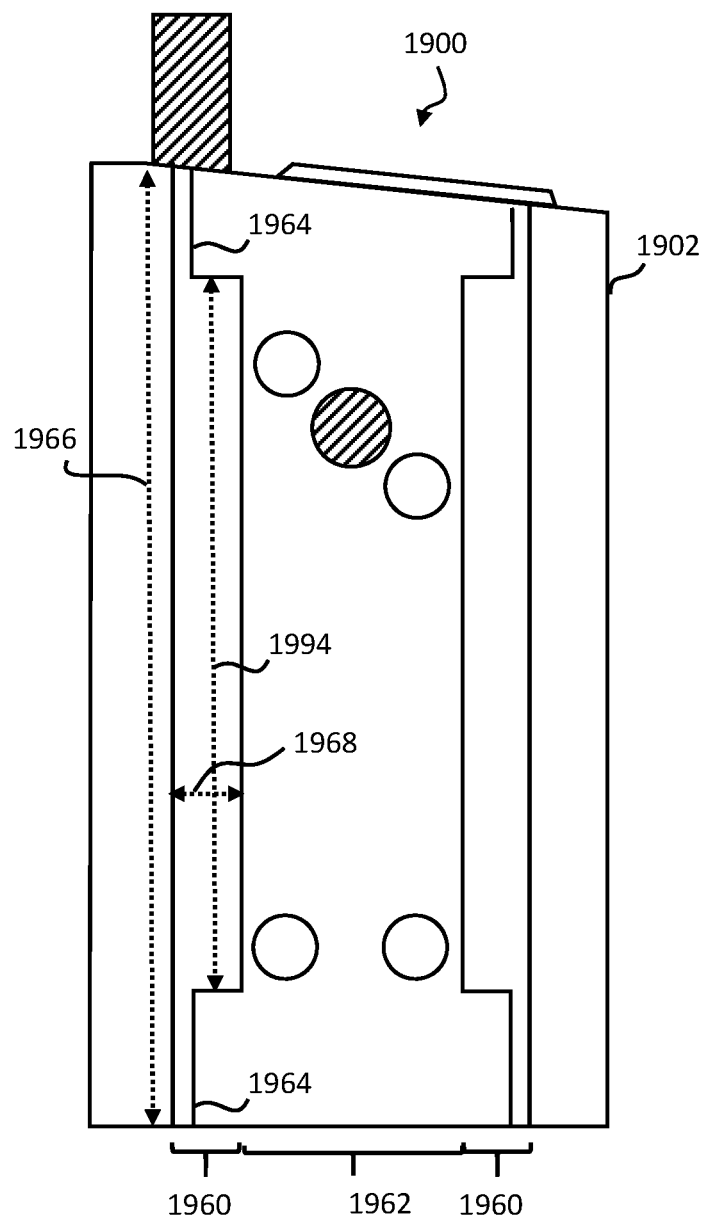
FIG. 19 shows a front view of another example aerosol provision system comprising an irregularly shaped first portion recessed with respect to a second portion.

FIG. 19 depicts another system 1900 comprising an assembly without a removable member attached thereto. This system substantially corresponds to that depicted in FIG. 5. This example differs from that described in FIG. 18 in that it comprises a first portion and second portion with a different shape than FIG. 18, to reduce the thin material problem previously described. For example, rather than having one or more raised portions, the second portion can be shaped to cover the regions where the material below would otherwise be considered too thin for a recess to be formed therein.

In this example, the outer surface of the assembly 1902 comprises at least a first portion 1960 and a second portion 1962. The first portion 1960 is recessed with respect to the second portion 1962 so that the outer surface of the assembly may have a stepped profile. This stepped profile provides a fulcrum 1964, or pivot point, about which the removable member can rotate. In the example of FIG. 19, the fulcrum 1964 is discontinuous and is separated by a gap 1994. In this example, there are two recessed portions 1960, however in other examples there may be one or more recessed portions.

The first portion 1960 may have a defined length 1966 and depth. In this example the first portion is substantially "T" shaped, with a width 1968. In this example the width is defined as the largest width, rather than the narrower width. The second portion 1962 may have a length similar to that of the first portion. In this example, the second portion 1962 is substantially "I" shaped, or generally in the form a balbis, with the top and bottom serifs extending to cover four regions where the material below would otherwise be considered too thin for a recess to be formed therein. As can be seen, these regions correspond to those where the one or more raised portions 1890 are located in FIG. 18. The irregular shaped first and second portions are also depicted in FIG. 5. Thus, FIG. 5 also depicts the outer surface of the assembly comprising a first portion and a second portion, the first portion being recessed with respect to the second portion to provide a fulcrum about which the removable member can rotate.

The outer surface of the assembly may be formed from metal, such as aluminum or an aluminum alloy.

In some examples, such as those in FIGS. 10-15, the first portion may have a width of about 1.5 mm to about 3 mm and a depth of about 0.2 mm to about 0.4 mm. For example, the width may be 1 mm, 1.5 mm, 2 mm, 2.5 mm or 3 mm, and the depth may be 0.2 mm, 0.3 mm or 0.4 mm. In some examples, such as that shown in FIGS. 16 and 17, the first portion may have a width of about 5 mm to about 6 mm, and a depth of about 0.2 mm to about 0.4 mm. For example, the width may be 5 mm, 5.25 mm, 5.75 mm, or 6 mm, and the depth may be 0.2 mm, 0.3 mm or 0.4 mm. In some examples, such as that shown in FIG. 18, the first portion may have a width of about 5 mm to about 6 mm, and a depth of about 0.2 mm to about 0.4 mm. For example, the width may be 5 mm, 5.25 mm, 5.75 mm, or 6 mm, and the depth may be 0.2 mm, 0.3 mm or 0.4 mm.

In one particular configuration, the first portion has a width of about 5.5 mm and a depth of about 0.2 mm, which provides a soft feel when the removable member is rotated, rather than an abrupt rotation. In another particular configuration, the first portion has a width of about 3 mm and a depth of about 0.2 mm, which may provide an improved "feel" when the removable member is rotated, and the opposite edge of the removable member lifts up higher to allow easier removal. In another particular configuration, like that shown in FIG. 19, the first portion has a widest width of about 3 mm or 4 mm and a depth of about 0.4 mm.

In order to address various issues and advance the art, the entirety of this disclosure shows by way of illustration and example various embodiments in which the claimed invention may be practiced and which provide for a superior apparatus arranged to generate an inhalable medium. The advantages and features of the disclosure are of a representative sample of embodiments only, and are not exhaustive and/or exclusive. They are presented only to assist in understanding and teach the claimed and otherwise disclosed features. It is to be understood that advantages, embodiments, examples, functions, features, structures and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist in essence of, various combinations of the disclosed elements, components, features, parts, steps, means, etc. The disclosure may include other inventions not presently claimed, but which may be claimed in future.

The invention claimed is:

1. An aerosol provision system, comprising:

an assembly defining an opening configured to receive a replaceable consumable; and a removable member releasably engaged with the assembly, the removable member conforming to and covering an outer surface of the assembly and configured to form part of an outer surface of the aerosol provision system, and positioned so as not to obstruct the opening, wherein the outer surface of the assembly comprises a first portion and a second portion, the first portion being recessed with respect to the second portion to provide a stepped profile about which the removable member can rotate; and an edge of the removable member is configured to rotate into the recessed first portion upon application of a force to a location on the removable member above and towards the recessed first portion to allow removal of the removable member.

2. The aerosol provision system according to claim 1, wherein the first portion being recessed with respect to the second portion k provides a fulcrum about which the removable member can rotate.

3. The aerosol provision system according to claim 2, wherein the first portion is dimensioned to receive the edge of the removable member as the removable member rotates about the fulcrum such that an opposite edge of the removable member rotates away from the second portion.

4. The aerosol provision system according to claim 3, wherein the outer surface of the assembly comprises a third portion, the second portion being recessed with respect to the third portion by a depth dimension substantially equal to a thickness dimension of the removable member.

5. The aerosol provision system according to claim 4, wherein the first portion is dimensioned such that an opposite edge of the removable member extends above the third portion as the removable member rotates about the fulcrum.

6. The aerosol provision system according to claim 3, wherein the removable member is attached to the assembly by one or more attachment elements and at least one of the one or more attachment elements is configured to detach as the removable member rotates about the fulcrum.

7. The aerosol provision system according to claim 6, wherein the one or more attachment elements are magnets arranged on the second portion.

8. The aerosol provision system according to claim 7, wherein a first magnet is arranged to engage the removable member at a first region, and a second magnet is arranged to engage the removable member at a second region, the second region being:

closer to an opposite edge than the first region; and closer to a midpoint of a length dimension of the removable member than the first region.

9. The aerosol provision system according to claim 2, wherein the first portion comprises one or more sections which are raised above a base of the first portion.

10. The aerosol provision system according to claim 2, wherein the first portion has a width dimension of about 1.5 mm to about 5.75 mm.

11. The aerosol provision system according to claim 2, wherein the first portion is recessed with respect to the second portion by a depth dimension of about 0.2 mm to about 0.4 mm.

12. The aerosol provision system according to claim 1, wherein at least one of the removable member and the assembly comprises an attachment element to attach the removable member to the assembly.

13. The aerosol provision system according to claim 12, wherein the assembly comprises the attachment element and the attachment element comprises a magnet.

14. The aerosol provision system according to claim 12, wherein the attachment element is configured to be slidably received within a channel.

15. The aerosol provision system according to claim 1, wherein at least a portion of an external surface of the removable member comprises a gripping surface, the gripping surface comprising raised portions.

16. A removable member configured for use with the aerosol provision system of claim 1.

17. A member to form part of an aerosol provision system, wherein the member is configured for releasable attachment to an outer surface of an aerosol provision assembly and defines an aperture through which a control element of the aerosol provision assembly is accessible in use, wherein the member is configured to rotate about a stepped profile defined by a first portion of the outer surface of aerosol provision assembly being recessed with respect to a second portion of the outer surface aerosol provision assembly, and, an edge of the member is configured to rotate into the recessed first portion upon application of a force to a location on the member above and towards the recessed first portion to allow removal of the member.

18. The member according to claim 17, wherein the member comprises magnetic material.

19. The member according to claim 17, wherein the member comprises an attachment element for engaging the aerosol provision assembly, and wherein the attachment element comprises an elongate member configured to be slidably received in a channel defined by a surface of the aerosol provision assembly.

20. The member according to claim 17, wherein the member comprises an attachment element for engaging the aerosol provision assembly, and wherein the attachment element comprises a channel defined by a surface of the member, the channel configured to slidably receive an elongate member formed on a surface of the aerosol provision assembly.

* * * * *